(12) United States Patent
Bielefeld (10) Patent No.: US 10,660,756 B2
(45) Date of Patent: May 26, 2020

(54) APPARATUS AND METHOD FOR HEART VALVE REPAIR

(71) Applicant: St. Jude Medical, LLC, Abbott Park, IL (US)

(72) Inventor: Eric E. Bielefeld, Floyds Knobs, IN (US)

(73) Assignee: St. Jude Medical, LLC, Abbott Park, IL (US)

( * ) Notice: Subject to any disclaimer, the term of this patent is extended or adjusted under 35 U.S.C. 154(b) by 302 days.

(21) Appl. No.: 15/840,170

(22) Filed: Dec. 13, 2017

(65) Prior Publication Data

US 2018/0098851 A1    Apr. 12, 2018

Related U.S. Application Data

(62) Division of application No. 14/237,993, filed as application No. PCT/US2012/047296 on Jul. 19, 2012, now Pat. No. 9,872,770.
(Continued)

(51) Int. Cl.
*A61F 2/24*    (2006.01)
*A61B 17/068*    (2006.01)
(Continued)

(52) U.S. Cl.
CPC .......... *A61F 2/2487* (2013.01); *A61B 17/068* (2013.01); *A61B 17/10* (2013.01); *A61F 2/2442* (2013.01); *A61B 2017/00243* (2013.01); *A61B 2017/00349* (2013.01); *A61B 2017/00783* (2013.01); *A61B 2017/0649* (2013.01); *A61B 2017/1103* (2013.01);
(Continued)

(58) Field of Classification Search
CPC .... A61B 2017/0649; A61B 2017/1103; A61B 17/12009; A61B 17/12013; A61B 17/0218; A61B 2017/00349; A61B 2017/1135; A61F 2/2487; A61F 2002/249; A61F 2/2463
See application file for complete search history.

(56) References Cited

U.S. PATENT DOCUMENTS

2002/0072761 A1    6/2002  Abrams et al.
2004/0127913 A1    7/2004  Voss
(Continued)

OTHER PUBLICATIONS

International Search Report for Application No. PCT/US2012/047296 dated Jan. 25, 2013.

*Primary Examiner* — Thomas MvEvoy
(74) *Attorney, Agent, or Firm* — Lerner, David, Littenberg, Krumholz & Mentlik, LLP (57) ABSTRACT

A device and method for repairing a mitral valve leaflet 2, 3. The device 10 includes a body 16 having an annular wall 18 and at least one aperture 22 through the annular wall 18. A deployment assembly 24 mounted on the body includes at least one grasping wire 28 arranged for sliding movement in the aperture 22. Movement of the deployment assembly 24 to a deployed position relative to the body causes a free end of the grasping wire 28 to project out from the annular wall 18 through the aperture 22, and movement of the deployment assembly to a retracted position relative to the body causes the free end of the grasping wire 28 to not project out from the annular wall 18. In the deployed position, the grasping wire 28 may grasp and gather tissue of the leaflet 2,3.

6 Claims, 7 Drawing Sheets

Related U.S. Application Data

(60) Provisional application No. 61/522,430, filed on Aug. 11, 2011.

(51) Int. Cl.
    *A61B 17/10*     (2006.01)
    *A61B 17/00*     (2006.01)
    *A61B 17/064*     (2006.01)
    *A61B 17/11*     (2006.01)
    *A61B 17/29*     (2006.01)
    *A61B 90/00*     (2016.01)
    *A61B 17/34*     (2006.01)

(52) U.S. Cl.
    CPC ................. *A61B 2017/2932* (2013.01); *A61B 2017/3488* (2013.01); *A61B 2090/3925* (2016.02)

(56) References Cited

U.S. PATENT DOCUMENTS

| | | |
|---|---|---|
| 2005/0240202 A1 | 10/2005 | Shennib et al. |
| 2007/0010715 A1 | 1/2007 | Sixto et al. |
| 2008/0051819 A1 | 2/2008 | Chasmawala et al. |
| 2008/0058730 A1 | 3/2008 | Melsheimer |
| 2010/0324572 A1 | 12/2010 | Needleman et al. |
| 2012/0277742 A1* | 11/2012 | Laufer ................... A61B 17/30 606/45 |

* cited by examiner

APPARATUS AND METHOD FOR HEART VALVE REPAIR

CROSS-REFERENCE TO RELATED APPLICATIONS

The present application is a divisional of U.S. patent application Ser. No. 14/237,993, filed on Apr. 2, 2014, which application is a national phase entry under 35 U.S.C. § 371 of International Application No. PCT/US2012/047296, filed Jul. 19, 2012, published in English, which claims priority from U.S. Provisional Application No. 61/522,430, filed Aug. 11, 2011, entitled APPARATUS AND METHOD FOR HEART VALVE REPAIR, all of which are hereby incorporated herein by reference.

BACKGROUND OF THE INVENTION

The present invention is related to heart valve repair, and more particularly to devices, systems, and methods for repair of a heart valve leaflet.

Properly functioning heart valves can maintain unidirectional blood flow in the circulatory system by directional opening and closing, depending on the difference in pressure from one side of the valve to the other. The two atrioventricular valves (mitral and tricuspid valves) are multicusped valves that prevent backflow from the ventricles into the atria during systole. They are anchored to the wall of the ventricle by chordae tendinae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendinae may stretch and thus become too long, or the chordae tendinae may be ruptured. As a result, the valve does not close normally. As a result of being stretched, the unsupported valve leaflet bulges back, or "prolapses," into the left atrium like a parachute. Thus, as the ventricle contracts, the abnormal leaflet may be propelled backwards, beyond its normal closure line and into the left atrium, thereby allowing blood to return to the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

One aspect of the disclosure provides a device for repair of a heart valve leaflet. The device includes a body having an annular wall and at least one aperture through the annular wall. A deployment assembly is mounted in the body and includes at least one grasping wire arranged for sliding movement in the at least one aperture. The deployment assembly has a deployed position in which a free end of the at least one grasping wire projects out from the annular wall through the at least one aperture. The deployment assembly also has a retracted position in which the free end of the at least one grasping wire does not project out from the annular wall.

In one example, the annular wall includes a plurality of apertures and the deployment assembly includes a plurality of grasping wires. In this example, each grasping wire being associated with a corresponding aperture so that in the deployed position, a free end of each grasping wire projects out from the annular wall through an associated aperture, and in the retracted position, the free end of each grasping wire does not project out from the annular wall. In one alternative, each of the apertures extends through the annular wall at an angle having a component in the radial direction of the body and a component in the circumferential direction of the body, and each of the angles are substantially equal. In another example, the grasping wire has a transverse cross-section with a width and a height, the width being greater than the height. In another example, the grasping wire has a rounded cross section. In another example, the aperture extends through the annular wall at an angle having a component in the radial direction of the body and a component in the circumferential direction of the body. In another example, the deployment assembly further includes a control rod rotatably mounted in the body. In this example, rotation of the control rod relative to the body in a first direction moves the deployment assembly from the retracted position to the deployed position, and rotation of the control rod relative to the body in a direction opposite the first direction moves the deployment assembly from the deployed position to the retracted position.

Another aspect of the disclosure provides a system for repair of a heart valve leaflet. The system includes a body having an annular wall and at least one aperture through the annular wall. A deployment assembly is mounted in the body, and includes at least one grasping wire arranged for sliding movement in the at least one aperture. The deployment assembly has a deployed position in which a free end of the at least one grasping wire projects out from the annular wall through the at least one aperture, and a retracted position in which the free end of the at least one grasping wire does not project out from the annular wall. The system also includes a shaft mounted over the body including a pushing member. The shaft is slidable and rotatable relative to the body. A helical clip is assembled over the body and engageable by the pushing member. Rotation of the shaft relative to the body rotates the helical clip about the body.

In one example, the helical clip comprises a coil having at least 1 turn. In another example, the helical clip includes at least one barb positioned along a length of the clip. In another example, the helical clip is in the form of a coil having an internal diameter, and the body has an external diameter. In this example, the internal diameter is no greater than the external diameter. In another example, the system also includes a sheath disposed over the shaft and the clip. In this example, the sheath has inner surface with threads and the shaft having an outer surface with threads complementary to the threads of the sheath. In another example, the annular wall includes a plurality of apertures and the deployment assembly includes a plurality of grasping wires. In this example, each grasping wire is associated with a corresponding aperture so that in the deployed position, a free end of each grasping wire projects out from the annular wall through an associated aperture, and in the retracted position, the free end of each grasping wire does not project out from the annular wall. In another example, the grasping wire has a transverse cross-section with a width and a height, the width being greater than the height. In another example, the free end of the at least one grasping wire projects out from the annular wall by at least 1 mm in the deployed position. In another example, the deployment assembly further includes a control rod rotatably mounted in the body, rotation of the control rod relative to the body in a first direction moving the deployment assembly from the retracted position to the deployed position. In this example, rotation of the control rod relative to the body in a direction opposite the first direction moves the deployment assembly from the deployed position to the retracted position.

Yet another aspect of the disclosure provides a device for repair of a heart valve leaflet. The device includes an elongated body having a distal portion including a grasping wire projecting laterally out from the body. A shaft is mounted over the body and includes a pushing member, the shaft being slidable and rotatable relative to the body. A helical clip is assembled over the body and engageable by the pushing member, such that rotation of the shaft relative to the body rotates the helical clip about the body.

In one example, the helical clip comprises a coil having at least 1 turn. In another example, the helical clip includes at least one barb positioned along a length of the clip. In another example, the helical clip is in the form of a coil having an internal diameter, and the body has an external diameter, the internal diameter is no greater than the external diameter. In another example, the device also includes a sheath slidably disposed over the shaft and the clip, the sheath having an internal surface with threads and the shaft having an outer surface with threads complementary to the threads of the sheath.

A further aspect of the disclosure provides a method for repair of a heart valve leaflet of a patient. The method includes positioning a repair device adjacent the heart valve leaflet. The repair device includes a body having an annular wall and at least one aperture through the annular wall. A deployment assembly is mounted in the body and including at least one grasping wire arranged for sliding movement in the at least one aperture. The deployment assembly is moved from a retracted position in which a free end of the at least one grasping wire does not project out from the annular wall to a deployed position in which the free end of the at least one grasping wire projects out from the annular wall through the at least one aperture. The body is rotated against the heart valve leaflet such that the at least one grasping wire grasps the heart valve leaflet and winds a portion of the heart valve leaflet around the body.

In one example, the repair device further includes a shaft mounted over the body and including a pushing member, and a helical clip assembled over the body. In this example, the method also includes sliding the shaft, and the helical clip over the body towards the portion of the wound heart valve leaflet and rotating the shaft relative to the body so that the pushing member engages a proximal end of the helical clip and rotates the helical clip. This causes a distal end of the helical clip to penetrate the wound portion of the heart valve leaflet. In another example, the method also includes releasing the proximal end of the clip from engagement with the pushing member when a distal end of the shaft contacts the wound portion of the heart valve leaflet. In another example, the method also includes moving the deployment assembly from the deployed position to the retracted position and withdrawing the body from the patient. In one alternative, the repair device further includes a sheath disposed over the shaft and the clip, the sheath having an inner surface with first threads and the shaft having an outer surface with threads complementary to the first threads on the sheath. In this alternative, the method also includes rotating the shaft relative to the sheath to advance the shaft and the clip toward the wound portion of the heart valve leaflet. In an alternative, the sheath has a proximal end and a distal end, the inner surface of the sheath adjacent the distal end includes at least one partial thread, and the clip is matingly engaged with the at least one partial thread. In this alternative, the step of rotating the shaft relative to the sheath rotates the clip relative to the sheath to release the clip from the at least one partial thread and from the sheath.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
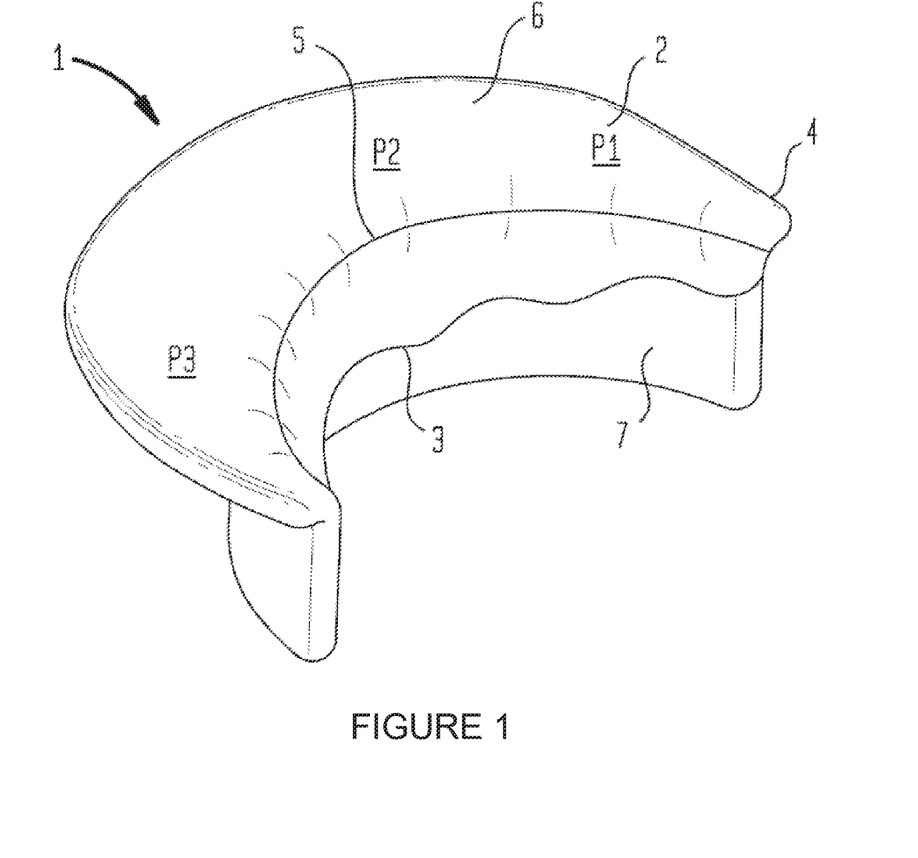
FIG. 1 is a diagrammatic perspective view of the posterior leaflet of a mitral valve.

As shown in FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus 4 and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore the cause of a prolapse condition of the valve. The inventive devices, systems, and methods described herein may be adapted to repair such a billowed, loose, or floppy portion of the posterior leaflet 2 or the anterior leaflet 3.

Figure 2:
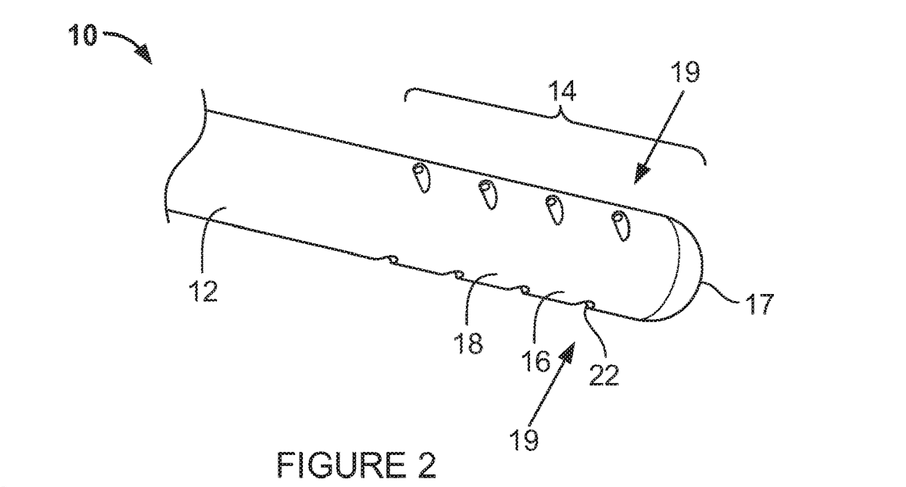
FIG. 2 is a perspective view of a distal portion of a device for repairing mitral valve leaflets in accordance with the present invention.

Referring to FIG. 2, an exemplary device 10 for repair of heart valve leaflet tissue may include an elongated body or catheter assembly 12 adapted to be inserted into the left atrium of a human heart so that a distal portion 14 of the catheter assembly may reach the patient's mitral valve for repair thereof.

The catheter assembly 12 may include a tubular body 16 having an annular wall 18 which extends from a tip 17 at the distal end of the tubular body to an operating handle (not shown) at the proximal end of the tubular body. Tip 17 may be a closed tip, as shown, or an open tip that may allow tubular body 16 to slide over a guide wire (not shown). In the distal portion 14 of catheter assembly 12, annular wall 18 may include a plurality of apertures 22. The apertures 22 may be arranged in rows 19 extending around the circumference of the tubular body 16. Although FIG. 2 shows four such rows 19, the tubular body 16 may include only a single row or any number of rows greater than one. Each row 19 may include one aperture 22, or any number of apertures greater than one. In preferred embodiments, tubular body includes 2-6 rows of apertures, with 2-4 apertures in each row. The apertures 22 in each row 19 may be evenly spaced around the circumference of tubular body 16, and may be aligned with one another in the longitudinal direction of the tubular body, as show in FIG. 2, or the apertures in one row may be circumferentially offset from the apertures in the next adjacent row. Moreover, the apertures 22 need not be arranged in rows at all, but may be arranged in any pattern or no particular pattern as desired.

Apertures 22 may extend through annular wall 18 at an oblique angle, forming a directional opening with components in both a radial direction and a circumferential direction of the tubular body. Optionally, the directional opening of apertures 22 may also include a component in the longitudinal direction of tubular body 16. Preferably, each aperture 22 is oriented in the same general direction relative to tubular body 16, and more preferably at substantially the same angle relative to the tubular body.

Figure 3:
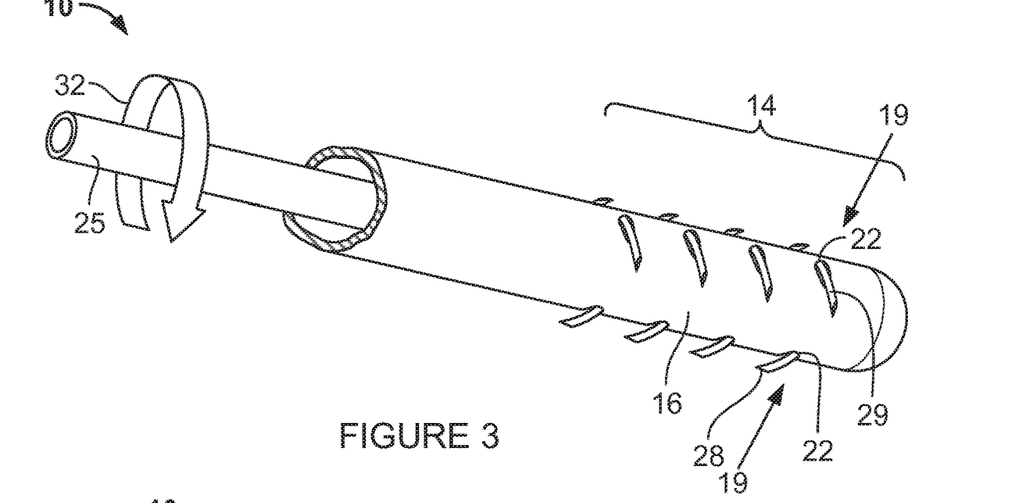
FIG. 3 is a perspective view of the device of FIG. 2 in a deployed position.
Figure 4:
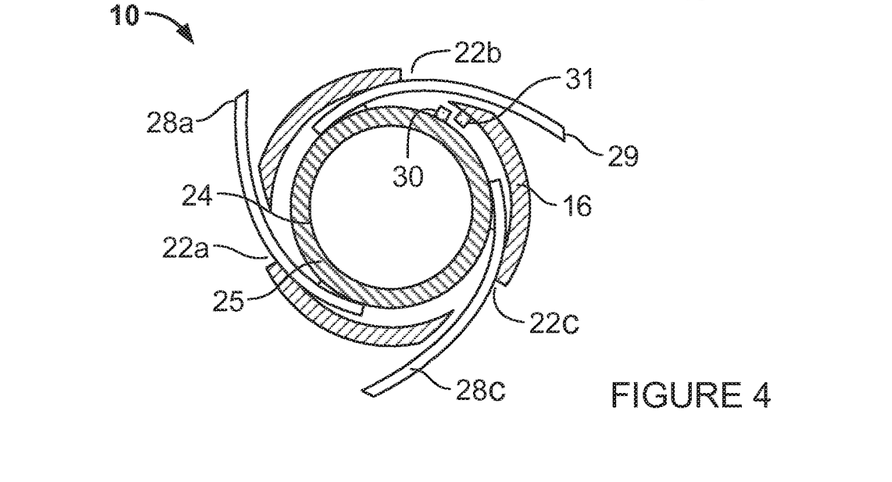
FIG. 4 is a transverse cross-sectional view of the device of FIG. 3.

FIG. 3 is a perspective view of device 10 in an open or deployed position, and illustrating a deployment assembly 24 rotatably mounted within tubular body 16, and FIG. 4 is a cross-sectional view through a central plane of one of the apertures of the device through the distal portion 14 of the catheter assembly 12. The deployment assembly 24 includes an elongated control rod 25 extending from the distal portion 14 of catheter assembly 12 to the operating handle thereof. Control rod 25 may have a solid or tubular structure. A plurality of grasping wires 28 may be mounted to a distal portion of the control rod 25 so as to project substantially tangentially therefrom. That is, each grasping wire 28 may be connected at one end to control rod 25, such as by welding, adhesive binding, mechanical fastener or the like, and may project freely from the connected end to a free end or tip 29. Tip 29 may be blunt or rounded. In a preferred arrangement, control rod 25 includes one grasping wire 28 for each aperture 22 formed in tubular body 16. Grasping wires 28 have cross-sectional dimensions which are slightly smaller than the dimensions of apertures 22 so that each grasping wire can slide outwardly and inwardly through an aperture without binding. The grasping wires 28 are preferably connected to control rod 25 in positions relative to the positions at which apertures 22 are provided in tubular body 16 so that the tip 29 of each grasping wire can be aligned with a corresponding aperture. For example, as shown in FIG. 4, aperture 22a corresponds to grasping wire 28a, aperture 22b corresponds to grasping wire 28b, and aperture 22c corresponds to grasping wire 28c.

The deployment assembly 24 may be rotatable within the tubular body 16 between a retracted position and a deployed position. In the retracted position (shown in FIG. 2), the tips 29 of grasping wires 28 reside within a corresponding aperture 22, but do not project outwardly from the annular wall 18. In that regard, a boss or other projection 30 on control rod 25 may interfere with a rib or other projection 31 on the interior surface of tubular body 16 to define the fully retracted position of the deployment assembly 24 and prevent the deployment assembly from rotating further relative to the tubular body 16 in the retraction direction. In one example, a weld joint between grasping wire 29 and deployment assembly 24 may interfere with an inner edge of the aperture and prevent further rotation of the deployment assembly relative to the tubular body. It will be appreciated, of course, that other arrangements may be provided for defining the fully retracted position of deployment assembly 24, including arrangements at the operating handle of catheter assembly 12. Providing a fixed stop in the retraction direction enables the grasping wires 28 to be retracted so as to not protrude from annular wall 18, but so that the tips 29 thereof remain within apertures 22 to facilitate deployment. Rotating the control rod 25 relative to the tubular body 16 in a direction opposite the retraction direction may move the grasping wires 28 through the directional openings of the corresponding apertures 22 and into the deployed position (shown in FIGS. 3 and 4). Each grasping wire 28 may have a round or a wide flat shape that moves through the directional opening of the corresponding aperture 22 according to the angle of the directional opening. When the deployment assembly 24 is in the deployed position, the grasping wires 28 may project outwardly at an angle from the annular wall 18. Grasping wires 28 preferably project out from annular wall 18 by an amount sufficient to grasp and gather the tissue of the medial valve leaflet 2, but not by an amount that is so long that it will simply flex backward without gathering tissue as the deployment assembly 24 is rotated. In preferred embodiments, the length of each grasping wire 28 that projects out from annular wall 18 will be between about 1 mm and about 4 mm.

As noted above, the deployment assembly 24 may be deployed by rotating the control rod 25 relative to the tubular body 16. This may be accomplished by holding the tubular body 16 stationary as the control rod 25 is rotated in a deployment direction, such as shown by direction arrow 32 in FIG. 3. Alternatively, deployment may be achieved by holding the control rod 25 stationary while tubular body 16 is rotated in a direction opposite that of directive arrow 32. In another alternative, tubular body 16 and control rod 25 may be rotated in opposing directions in order to move grasping wires 28 to the deployed condition.

Once in the deployed condition, a detent, ratchet or other structure (not shown) may releasably lock the deployment assembly 24 relative to the tubular body 16 in order to prevent the deployment assembly from inadvertently or undesirably rotating relative to the tubular body in an opposite direction and returning to the retracted position. Accordingly, when not locked, the control rod 25 and/or the tubular body 16 may be rotated in the direction opposite the first direction. This may cause grasping wires 28 to retract back through apertures 22 to the fully retracted position.

Figure 6:
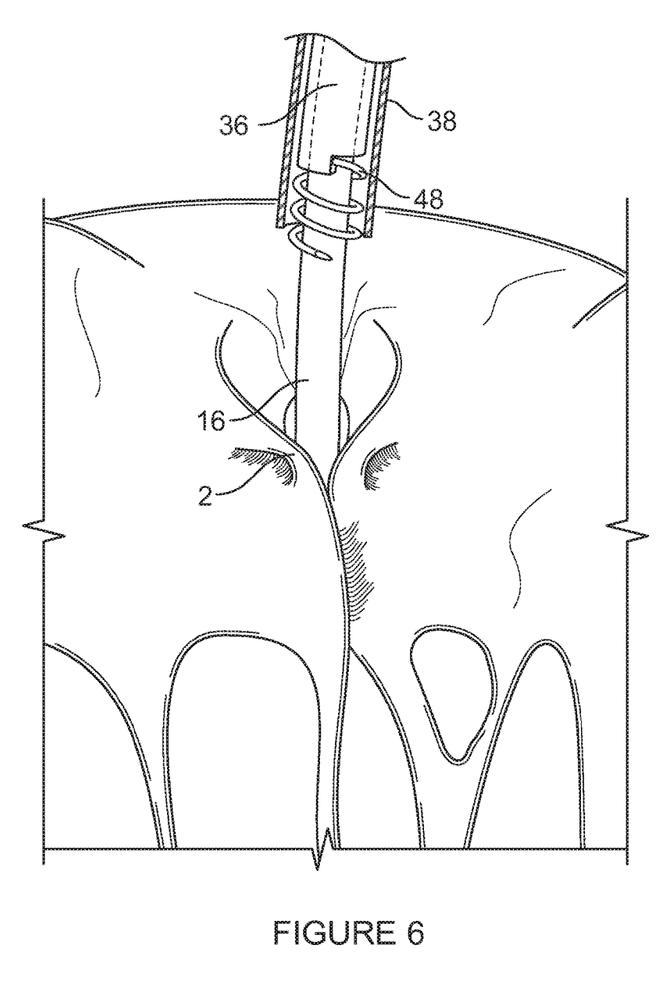

In order to hold the tissue of leaflet 2 in the gathered condition, device 10 may include a mechanism for applying a clip 48, described below, to the gathered tissue. The mechanism may include a shaft 36 rotatably and slidably disposed over tubular body 16 and within an outer sheath 38, all of which is shown in FIG. 6. The outer surface of the rotatable shaft 36 may include serrations or threads that may mate with complementary threads on the inner surface of sheath 38. At its distal end, shaft 36 may be formed with a notch 37 sized to engage the proximal end of clip 48. The shaft 36 and sheath 38 may be slid together over tubular body 16 towards the distal portion 14 of the catheter assembly and also proximally away from the distal portion 14. With the sheath 38 held in place, the rotation of shaft 36 within the sheath will cause the shaft to move distally or proximally along tubular body 16, depending on the direction of rotation. Movement of shaft 36 distally will drive the clip 48 into the gathered tissue, as will be described more fully below.

Figure 8:
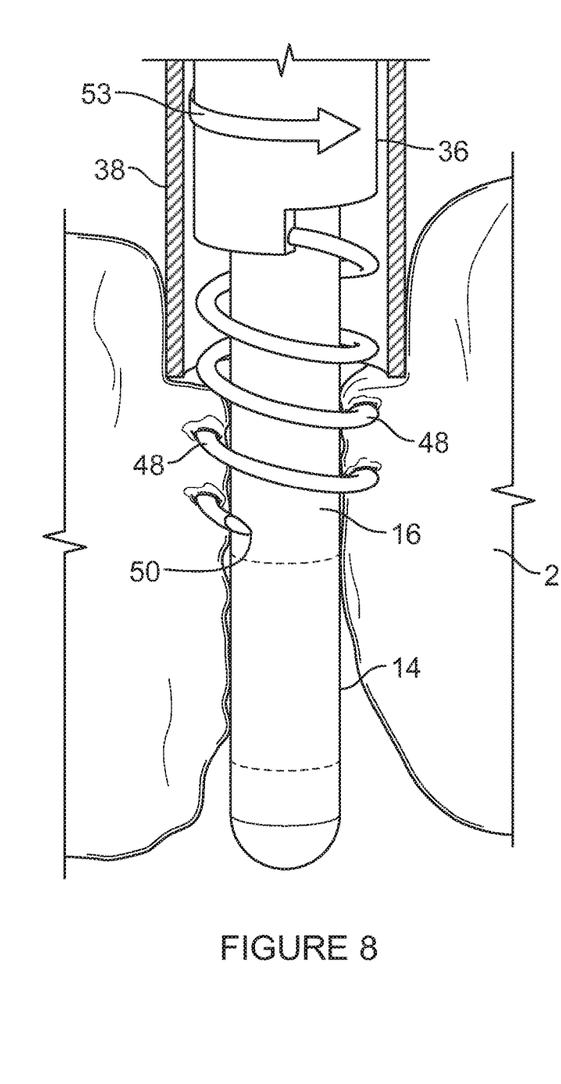
Figure 9A:
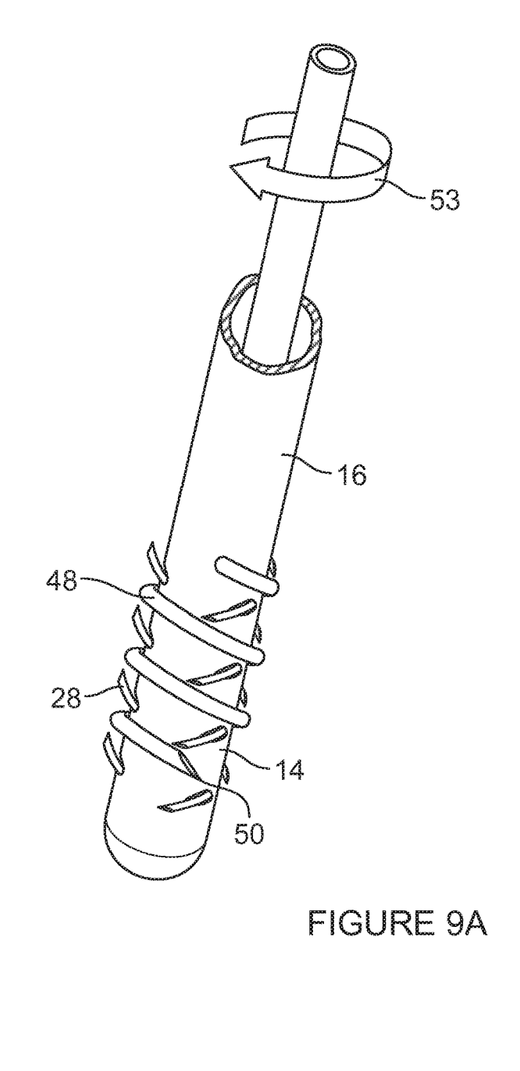
FIGS. 9A and 9B are further illustrations of steps for repairing a mitral valve leaflet using the device of FIG. 2.
Figure 9B:
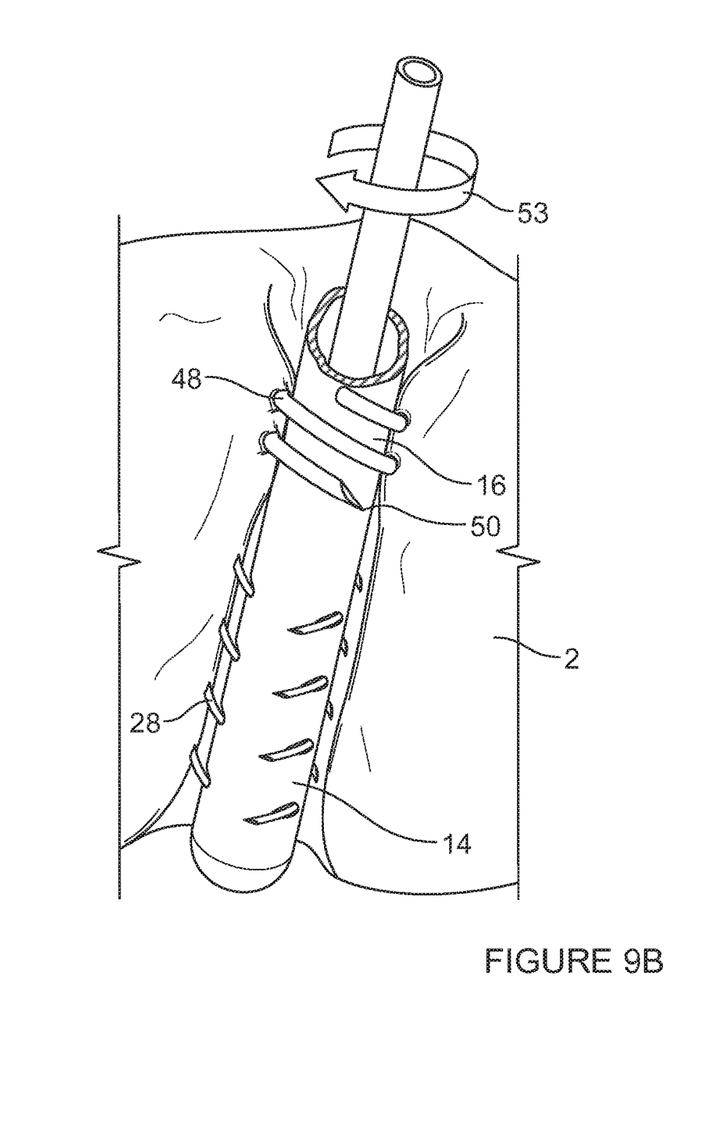

Referring to FIG. 8, clip 48 has a coiled configuration formed by one or more helical turns of a wire. Preferably, clip 48 includes at least two complete turns of wire. The distal end 50 of clip 48 may be sharpened to facilitate the piercing of leaflet tissue as the clip is advanced distally. Clip 48 preferably has an inner diameter D that is similar to the diameter of tubular body 16 so that the clip engages the tubular body with a weak frictional force that will hold the clip in place on the tubular body, but that can be overcome to advance the clip down the length of the tubular body as shaft 36 is rotated. Alternatively, tubular body 16 may be designed so that the positions of apertures 22, and hence the positions of grasping wires 28 in the deployed position, enable clip 48 to be "threaded" between the grasping wires as the clip is advanced distally as shown in FIG. 9A. In another alternative, shown in FIG. 9B, if tissue is twisted tightly against tubular body 16, clip 48 may penetrate the tissue proximal to the grasping wires, and the clip may stop before distal end 50 reaches the grasping wires of the tubular body 16. In yet another alternative, sheath 28 may include a small amount of threads, for example, one turn or less, at its distal end. These threads may hold the clip 48 within the sheath while the shaft 36 is rotated and until the clip 48 has contacted and/or pierced the valve leaflet tissue. Once the clip 48 is released from the threads of the sheath 38, the clip may expand in dimension around the grasping wires.

The use of device 10 to gather the loose tissue of a mitral valve leaflet and to apply a clip 48 to the gathered tissue will now be described with reference to FIGS. 5-8, 9a, 9B, and 10. Initially, device 10 is placed in a starting condition with a clip 48 mounted on tubular body 16, the clip and rotatable shaft 36 in a fully retracted position within outer sheath 38, and deployment assembly 24 in the fully retracted position. With device 10 in this starting condition, the catheter assembly 12 may be inserted into the patient and advanced to the mitral valve, preferably using a transseptal approach. That is, the catheter assembly 12 may be inserted into the femoral vein, and advanced from there through the iliac vein, the inferior vena cava, and the right atrium, and through the septum wall into the left atrium until the distal portion 14 thereof extends between the posterior leaflet 2 and the anterior leaflet 3 of the mitral valve 1. This route minimizes the bending and twisting of the catheter assembly 12 and thereby facilitates the rotational control over the various components thereof. If the distal portion 14 includes echogenic materials, it may be guided to a position against a leaflet at the coaption line 5 using the assistance of three-dimensional echocaradiography to visualize the distal portion and other components of the device 10.

Once the device 10 has reached the leaflets 2 and 3, the control rod 25 may be rotated in the direction of arrow 32 to move deployment assembly 24 to the deployed position in which grasping wires 28 extend out from the apertures 22 in tubular body 16. The control rod 25 may be rotated until deployment assembly 24 becomes locked in the deployed position relative to the tubular body 16.

Figure 5:
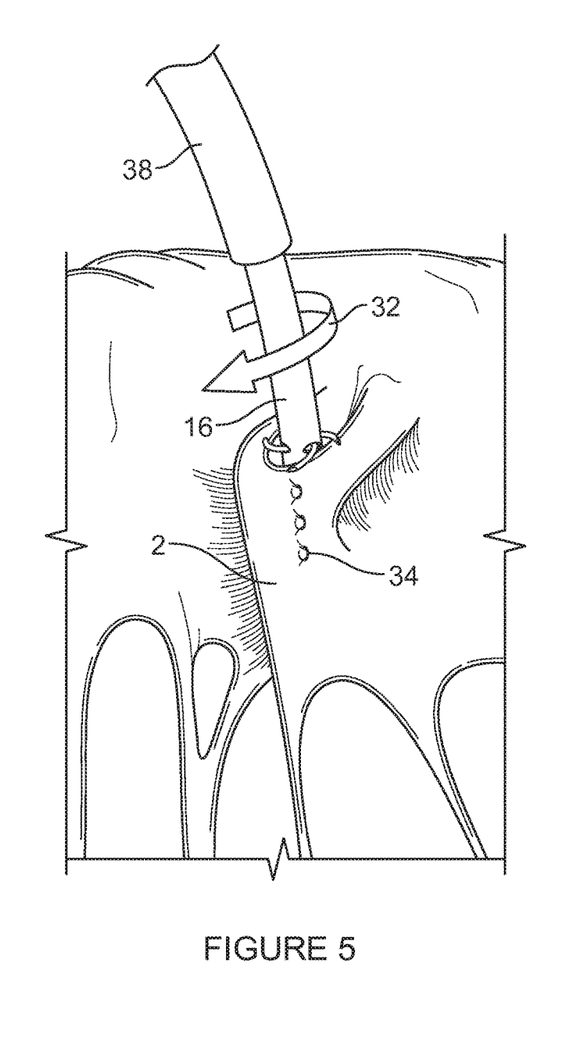
FIGS. 5-8 are illustrations of the sequence of steps for repairing a mitral valve leaflet using the device of FIG. 2.

As shown in FIG. 5, with the distal portion 14 positioned against the leaflet 2, continued rotation of control rod 25 in the direction of arrow 32 will result in the rotation of tubular body 16, and with it grasping wires 28. This rotation may cause the grasping wires 28 to grip or grab tissue of leaflet 2 and wind the tissue around the outer surface of the tubular body 16. The blunt or rounded tips 29 of grasping wires 28 may prevent piercing of the tissue. In another example, if grasping wires 28 include sharpened tips, the sharpened ends may skewer the tissue, thereby bunching and twisting the tissue as the control rod 25 is rotated. The bumps or protrusions 34 shown in the surface of leaflet 2 may be caused by the grasping wires 28 grabbing the tissue.

Figure 7:
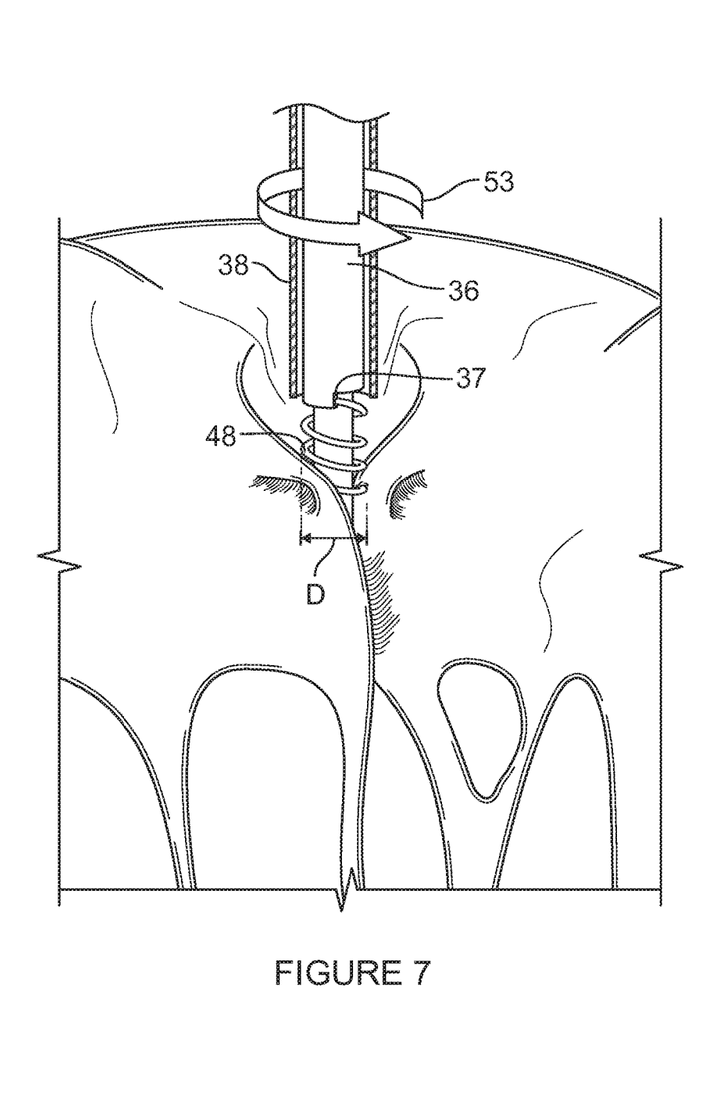

When a desired amount of the tissue of leaflet 2 has been wound around the tubular body 16, device 10 may be operated to apply a clip 48 to the gathered tissue. As an initial step, the rotatable shaft 36, sheath 38, and clip 48 may be slid together distally along tubular body 16, with the shaft and clip in the retracted position within the sheath, until the distal end of the shaft contacts or is adjacent to the leaflet tissue gathered on the distal portion 14 of the tubular body. The shaft 36 may then be rotated (as indicated by direction arrow 53 in FIG. 7) within the sheath 38 such that the threaded engagement between the shaft and the sheath causes the shaft 36 to move distally relative to the sheath. The distal movement of shaft 36 will cause clip 48 to also move distally along tubular body 16, with the engagement of the proximal end of the clip with the notch 37 causing the clip to rotate as it advances. As shown in FIG. 7, the shaft 36 may be rotated in a direction opposite of the rotation of control rod 25 (arrow 32 of FIG. 5) to gather and twist the leaflet tissue. Accordingly, the pitch of coil 48 may be the reverse of the rotation of the control rod 25. If coil 48 were to turn in the same direction as control rod 25 of FIG. 5, the coil may push the tissue off of the control rod. Thus, preferably, coil 48 may be turned in a direction opposite of the control rod 25 when gathering the tissue so that the rotational forces oppose one another and the coil 48 may be driven into the gathered tissue. As the clip 48 advances distally out from sheath 38 and approaches the gathered tissue, the combined advancement and rotation of the clip will cause the sharpened distal end 50 thereof to pierce the tissue.

The continued rotation of the shaft 36 may drive the clip 48 into and through the gathered tissue surrounding the distal end 14 of tubular body 16. For example, as shown in the partial cut-away view of FIG. 8 (the details of the grasping wire, apertures, etc. of the distal portion 14 not being shown for clarity), two full turns of the clip 48 have progressed through the gathered tissue.

Figure 10:
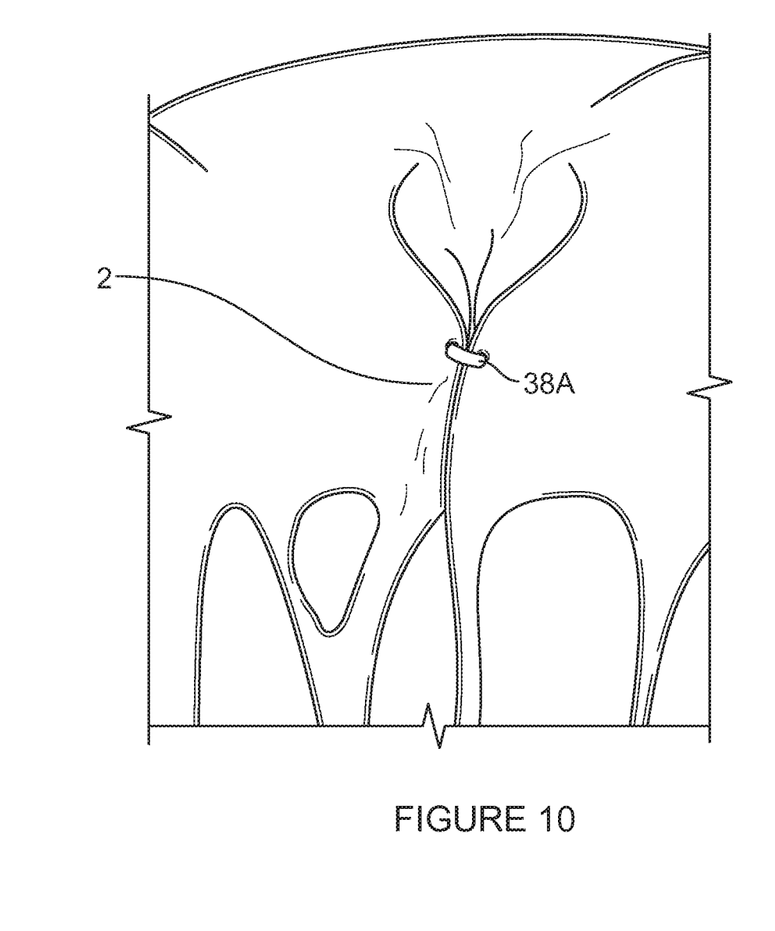
FIGS. 10 and 11 are illustrations of a repaired mitral valve leaflet.
Figure 11:
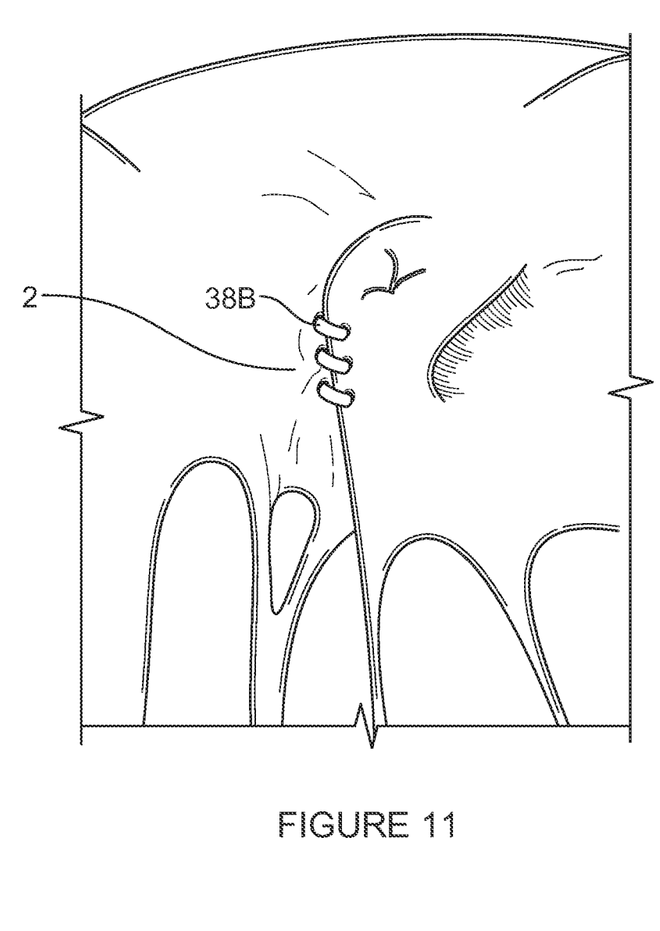

Once the distal end of shaft 36 has reached the gathered tissue of the leaflet 2, the notch 37 may no longer be able to drive the clip 48 further into the tissue. The helical shape of clip 48 may hold the tissue of the leaflet 2 in the gathered configuration. It will be understood that the dimensions, shape, and configuration of the clips may be varied depending upon the needs of the patient. For example, FIGS. 10 and 11 show two clips 38A and 38B, respectively, holding the tissue of leaflet 2 in a gathered configuration. In the examples, clip 38A includes one or two turns while clip 38B includes three or four turns. The winding of the leaflet 2 around tubular body 16 may change the shape of the leaflet, tightening loose or floppy tissue. This tightening of the tissue may reduce the likelihood of prolapse and mitral valve regurgitation, thereby repairing the functionality of the valve.

Once clip 48 is securely in place, the catheter assembly 12, including the distal portion 14, the rotatable shaft 36, and the sheath 38, may be withdrawn from the patient at the point of entry. In order to do so, the control rod 25 is rotated in the direction opposite to the deployment direction, i.e., opposite to the direction of arrow 32. This action causes the gasping wires 28 to retract into the tubular body 16. Control rod 25 is rotated in this retraction direction until a stop is engaged at the fully retracted position and the control rod is unable to rotate further. At this point, the tips 29 of grasping wires 28 will reside within their corresponding apertures 22, freeing the grasping wires from engagement with the tissue, and enabling the catheter assembly 12 to be pulled proximally away from the gathered and clipped tissue.

Figure 12:
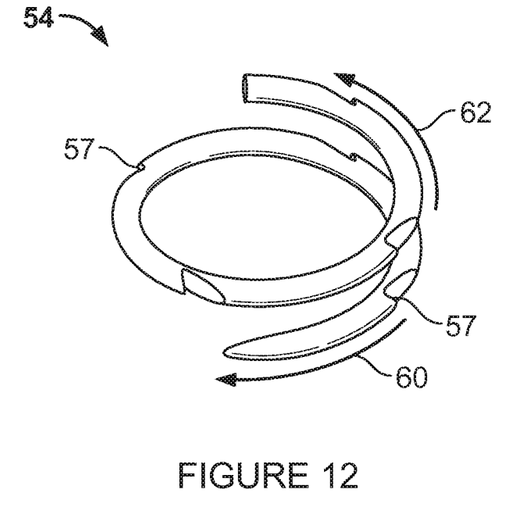
FIG. 12 is a perspective view of a coil clip for repairing and securing mitral valve leaflets in accordance with the present invention.

A clip 54 in accordance with a variant of the present invention is shown in FIG. 12. Clip 54 is substantially the same as clip 48 described above, but rather than the smooth, constant cross-section along the length of the wire forming the windings of clip 48, clip 54 includes one or more cutouts or barbs 57 oriented so as to prevent clip 54 from backing out of the leaflet tissue following deployment. That is, once clip 54 has been deployed in the leaflet tissue by rotating, for example, in the direction of arrow 60, any force tending to cause the clip to rotate in the opposite direction (for example, in the direction of arrow 62) may cause the barbs 57 to snag the tissue, preventing the clip from rotating out from the tissue. Although FIG. 12 shows all of barbs 57 oriented in the same direction, it will be appreciated that clip 54 may include one or more additional barbs (not shown) oriented in the opposite direction. Such additional barbs may prevent clip 54 from further rotating in the direction of arrow 60 subsequent to deployment. Since such additional barbs may snag on the leaflet tissue as clip 54 is deployed into the leaflet tissue, it is preferred that these barbs be positioned near the proximal end of the clip to minimize any damage to the tissue.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

INDUSTRIAL APPLICABILITY

The present disclosure can be used to repair heart valve leaflets.

The invention claimed is:

1. A method for repair of a heart valve leaflet of a patient, the method comprising:
   positioning a repair device adjacent the heart valve leaflet, the repair device including a body having an annular wall and at least one aperture through the annular wall, and a deployment assembly mounted in the body and including at least one grasping wire arranged for sliding movement in the at least one aperture;
   moving the deployment assembly from a retracted position in which a free end of the at least one grasping wire does not project out from the annular wall to a deployed position in which the free end of the at least one grasping wire projects out from the annular wall through the at least one aperture; and
   rotating the body against the heart valve leaflet such that the at least one grasping wire grasps the heart valve leaflet and winds a portion of the heart valve leaflet around the body.

2. The method of claim 1, wherein the repair device further includes a shaft mounted over the body, a pushing member, and a helical clip assembled over the body, the method further comprising:
   sliding the shaft and the helical clip over the body towards the wound portion of the heart valve leaflet; and
   rotating the shaft relative to the body so that the pushing member engages a proximal end of the helical clip and rotates the helical clip, whereby a distal end of the helical clip penetrates the wound portion of the heart valve leaflet.

3. The method of claim 2, further comprising releasing the proximal end of the clip from engagement with the pushing member when a distal end of the shaft contacts the wound portion of the heart valve leaflet.

4. The method of claim 3, further comprising:
   moving the deployment assembly from the deployed position to the retracted position; and
   withdrawing the body from the patient.

5. The method of claim 4, wherein the repair device further includes a sheath disposed over the shaft and the clip, the sheath having an inner surface with first threads and the shaft having an outer surface with threads complementary to the first threads on the sheath, the method further comprising:
   rotating the shaft relative to the sheath to advance the shaft and the clip toward the wound portion of the heart valve leaflet.

6. The method of claim 5, wherein the sheath has a proximal end and a distal end, the inner surface of the sheath adjacent the distal end includes at least one partial thread, and the clip is matingly engaged with the at least one partial thread, and the step of rotating the shaft relative to the sheath rotates the clip relative to the sheath to release the clip from the at least one partial thread and from the sheath.

* * * * *